United States Patent
Ihara et al.

(10) Patent No.: US 8,471,036 B2
(45) Date of Patent: Jun. 25, 2013

(54) RHODACYANINE DERIVATIVE AND PHARMACEUTICAL COMPOSITION FOR TREATING LEISHMANIASIS

(75) Inventors: Masataka Ihara, Tokyo (JP); Isamu Itoh, Tokyo (JP)

(73) Assignees: FUJIFILM Corporation, Tokyo (JP); Hoshi University, Tokyo (JP)

( * ) Notice: Subject to any disclaimer, the term of this patent is extended or adjusted under 35 U.S.C. 154(b) by 0 days.

(21) Appl. No.: 13/501,456

(22) PCT Filed: Oct. 6, 2010

(86) PCT No.: PCT/JP2010/067994
§ 371 (c)(1),
(2), (4) Date: May 11, 2012

(87) PCT Pub. No.: WO2011/046158
PCT Pub. Date: Apr. 21, 2011

(65) Prior Publication Data
US 2012/0220639 A1    Aug. 30, 2012

(30) Foreign Application Priority Data
Oct. 13, 2009    (JP) .................... 2009-251292

(51) Int. Cl.
*A61K 31/428* (2006.01)
*C07D 417/14* (2006.01)

(52) U.S. Cl.
USPC .......................................... 548/156; 514/367

(58) Field of Classification Search
USPC ........................................................ 548/156
See application file for complete search history.

(56) References Cited

U.S. PATENT DOCUMENTS
5,424,442 A * 6/1995 Koya et al. ............... 548/156

FOREIGN PATENT DOCUMENTS

| | | | |
|---|---|---|---|
| EP | 0452965 A | | 10/1991 |
| JP | 51/106425 A | * | 9/1976 |
| JP | 9-501653 A | | 2/1997 |
| JP | 11-106394 A | | 4/1999 |
| JP | 2001-226369 A | | 8/2001 |
| JP | 2003-034640 A | | 2/2003 |
| JP | 2004-331545 A | | 11/2004 |
| JP | 2006-104116 A | | 4/2006 |

OTHER PUBLICATIONS

J. Med. Chem., 2010, vol. 53, No. 1, p. 368-373, published on the web Nov. 6, 2009.
Extended European Search Report dated Mar. 6, 2013 from the EPO in European patent application corresponding to the instant patent application.

* cited by examiner

*Primary Examiner* — Laura L. Stockton
(74) *Attorney, Agent, or Firm* — SOLARIS Intellectual Property Group, PLLC

(57) ABSTRACT

A rhodacyanine derivative represented by the following General Formula (1), wherein, in General Formula (1), $R^1$, $R^2$, and $R^3$ each independently represent an alkyl group which may be substituted; $Y^1$ and $Y^2$ each independently represent a hydrogen atom, a chlorine atom, or a fluorine atom provided that $Y^1$ and $Y^2$ do not represent hydrogen atoms at the same time; and X represents a counter anion. A pharmaceutical composition for treating leishmaniasis including the rhodacyanine derivative and a pharmaceutically acceptable carrier.

(1)

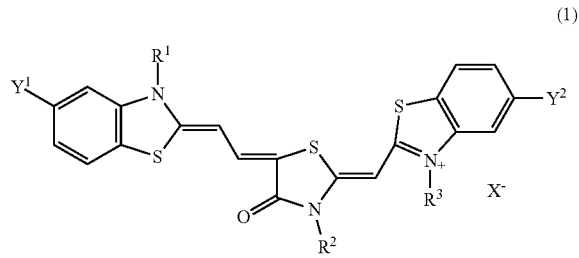

18 Claims, No Drawings

RHODACYANINE DERIVATIVE AND PHARMACEUTICAL COMPOSITION FOR TREATING LEISHMANIASIS

TECHNICAL FIELD

The present invention relates to a novel rhodacyanine derivative and a pharmaceutical composition for treating leishmaniasis.

BACKGROUND ART

Leishmaniasis is a tropical parasitic infectious disease caused by protozoa of the genus *Leishmania* parasitizing macrophages of a host such as a human, and is propagated mainly via sand flies living in the desert. The WHO (World Health Organization) has designated leishmaniasis as one of the six major tropical diseases. Patients thereof in Africa, Middle and Near East, Latin America, and Asia account for most of the worldwide patients (approximately 12 million people/year), and approximately 350 million people are threatened by infection thereof. Many of the people live in developing countries, and are hardly able to afford expensive drugs.

In the current treatment of leishmaniasis, pentavalent antimony formulations, such as pentostam, are used as first-line drugs. However, pentavalent antimony formulations are expensive, and side-effects caused by high toxicity thereof are problematic. Further, the emergence of drug-resistant protozoa has been confirmed in India, which poses a new serious problem. In a case in which antimony formulations may not be effective, diamidine compounds such as an isethionate salt of pentamidine (4,4'-(pentamethylenedioxy)dibenzamidine) are used (see, for example, Japanese National-Phase Patent Publication (JP-A) No. 9-501653), and macrolide antibiotics such as an antifungal antibiotic amphotericin B are secondarily used against fungal infection or mucocutaneous leishmaniasis. However, the efficacy of these diamidine compounds and amphotericin B is not as high as pentavalent antimony formulations. Further, these drugs are expensive, and various side-effects thereof have been reported.

Other known therapeutic drugs for leishmaniasis include antiprotozoal drugs containing germacrane and guaiane sesquiterpenoid compounds that have been extracted, purified, and separated from an Asteraceae plant (*Elephantopus mollis* H.B.K.) (see, for example, Japanese Patent Application Laid-open (JP-A) No. 2001-226369), and therapeutic drugs for leishmaniasis of which the active ingredient is a glucopyranose terpenoid derivative (see, for example, JP-A No. 11-106394). However, these therapeutic drugs have the drawback of low drug efficacy.

In recent years, it has been disclosed that rhodacyanine dyes of a certain type exhibit a strong cell-proliferation inhibiting activity against *leishmania* protozoa although the cytotoxicity thereof against mammalian cells, which is an index of side-effects, is low, and the rhodacyanine dyes thus have a high selective toxicity coefficient, and are effective as anti-*leishmania* agents (JP-A Nos. 2004-331545 and 2006-104116). However, results thereof in a *leishmania* protozoa proliferation inhibiting test in macrophages, and activity thereof in an experimental system in which a pathological model of infected animals is used, have not been reported.

SUMMARY OF INVENTION

Technical Problem

As described above, a compound which has high selective toxicity against parasitic leishmaniasis, and which is confirmed to have sufficiently high activity and sufficient efficacy as a pharmaceutical composition for treating leishmaniasis, has not been found.

An object of the present invention is provision of a novel pharmaceutical composition for treating leishmaniasis which has high selective toxicity against parasitic leishmaniasis, and which exhibits sufficiently high activity and sufficient efficacy against leishmaniasis.

Solution to Problem

According to the invention, the following rhodacyanine derivatives and pharmaceutical compositions for treating leishmaniasis are provided.

<1> A rhodacyanine derivative represented by the following General Formula (1):

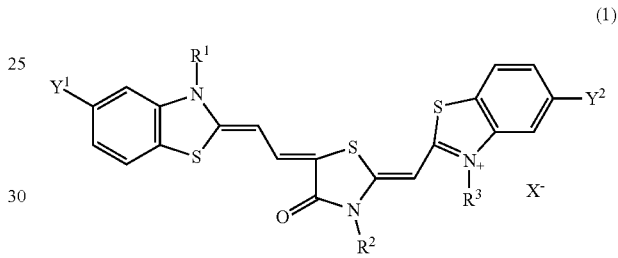

In General Formula (1), $R^1$, $R^2$, and $R^3$ each independently represent an alkyl group which may be substituted; $Y^1$ and $Y^2$ each independently represent a hydrogen atom, a chlorine atom, or a fluorine atom provided that $Y^1$ and $Y^2$ do not represent hydrogen atoms at the same time; and X represents a counter anion.

<2> The rhodacyanine derivative described in <1>, wherein, in General Formula (1), $R^1$, $R^2$, or $R^3$ represents an alkyl group having from 1 to 8 carbon atoms, wherein the alkyl group may be substituted.

<3> The rhodacyanine derivative described in <1> or <2>, wherein, in General Formula (1), $R^1$, $R^2$, or $R^3$ represents an alkyl group having at least one substituent selected from the group consisting of a halogen atom, a hydroxyl group, an oxo group, an alkyl group, an alkoxy group, and a carboxy group.

<4> The rhodacyanine derivative described in any one of <1> to <3>, wherein, in General Formula (1), X is selected from the group consisting of a halogen ion, a sulfonate ion, a sulfamate ion, a sulfate ion, a hydrogensulfate ion, a borate ion, an alkylphosphate ion, a dialkylphosphate ion, a pyrophosphate ion, a carboxylate ion, a carbonate ion, a hydrogencarbonate ion, and a hydroxide ion.

<5> The rhodacyanine derivative described in any one of <1> to <4>, wherein, in General Formula (1), at least one of $Y^1$ or $Y^2$ represents a fluorine atom, $R^1$ and $R^3$ each represent a methyl group, and $R^2$ represents an ethyl group.

<6> The rhodacyanine derivative described in <1>, wherein the rhodacyanine derivative is represented by the following Formula (2):

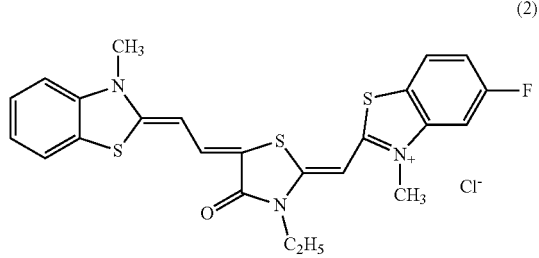 [SMILES: CCn1c(=O)/c(=C/C=C2\Sc3ccccc3N2C)s/c1=C\c1sc2ccc(F)cc2[n+]1C ; [Cl-]]

(2)

<7> A pharmaceutical composition for treating leishmaniasis, comprising the rhodacyanine derivative described in any one of <1> to <6> and a pharmaceutically acceptable carrier.
<8> A method of treating leishmaniasis, comprising administering the pharmaceutical composition for treating leishmaniasis described in <7> to a patient infected with *leishmania* or suspected to be infected with *leishmania*.
<9> A composition for use as a medicament, comprising the rhodacyanine derivative described in any one of <1> to <6> and a pharmaceutically acceptable carrier.

DESCRIPTION OF EMBODIMENTS

The rhodacyanine derivative according to the invention is a compound represented by the following General Formula (1). In General Formula (1), $R^1$, $R^2$, and $R^3$ each independently represent an alkyl group which may be substituted; $Y^1$ and $Y^2$ each independently represent a hydrogen atom, a chlorine atom, or a fluorine atom provided that $Y^1$ and $Y^2$ do not represent hydrogen atoms at the same time; and X represents a counter anion.

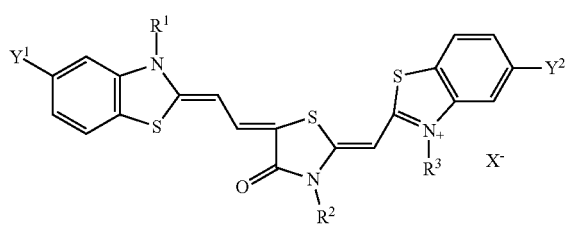

(1)

The present inventors have found the above rhodacyanine dye compound, which has a fluorine atom or a chlorine atom as a substituent, exhibits high efficacy against leishmaniasis and less side-effects in an experimental system in which a pathology model of an animal infected with *leishmania* protozoa is used. Thus, the inventors have completed the present invention. A pharmaceutical composition for treating leishmaniasis of which a main component is the above compound has high selective toxicity, and exhibits high activity and efficacy against leishmaniasis.

The invention is described in detail below.

Hereinafter, a numerical range expressed by "from X to Y" is inclusive of X and Y as the lower limit value and the higher limit value, respectively.

The rhodacyanine derivative according to the invention is a compound represented by General Formula (1), in which $R^1$, $R^2$, and $R^3$ each independently represent an alkyl group which may be substituted, $Y^1$ and $Y^2$ each independently represent a hydrogen atom, a chlorine atom, or a fluorine atom provided that $Y^1$ and $Y^2$ do not represent hydrogen atoms at the same time, and X represents a counter anion.

In the compound represented by General Formula (1), $R^1$, $R^2$, and $R^3$ each independently represent preferably an alkyl group having from 1 to 8 carbon atoms, wherein the alkyl group may be substituted. Specific examples of the alkyl group include a methyl group, an ethyl group, a propyl group, a butyl group, a pentyl group, a hexyl group, a heptyl group, and an octyl group.

The alkyl group represented by any of $R^1$, $R^2$, or $R^3$ may have one substituent, or two or more substituents. Examples of substituents include halogen atoms, a hydroxyl group, an oxo group, alkyl groups, alkoxy groups, and a carboxyl group, and examples of preferable substituents include halogen atoms, an oxo group, alkyl groups, alkoxy groups, and a carboxyl group. $R^1$, $R^2$, and $R^3$ each independently represent more preferably an unsubstituted alkyl group, and still more preferably a methyl group or an ethyl group. In a particularly preferable example for $R^1$, $R^2$, and $R^3$, $R^1$ and $R^3$ represent methyl groups and $R^2$ represents an ethyl group.

In the compound represented by General Formula (1), $Y^1$ and $Y^2$ each independently represent a hydrogen atom, a fluorine atom, or a chlorine atom. It is more preferable that at least one of $Y^1$ or $Y^2$ represents a fluorine atom, and it is particularly preferable that $Y^1$ represents a hydrogen atom and $Y^2$ represents a fluorine atom. However, $Y^1$ and $Y^2$ are not hydrogen atoms at the same time.

X in General Formula (1) represents a counter anion, which is not particularly limited. Preferable examples thereof include: halogen ions such as a chlorine ion, a bromine ion, and an iodine ion; sulfonate ions such as aliphatic and aromatic sulfonate ions, such as a methanesulfonate ion, a trifluoromethanesulfonate ion, a p-toluenesulfonate ion, a naphthalenesulfonate ion, and a 2-hydroxyethanesulfonate ion; sulfamate ions such as a cyclohexanesulfamate ion; sulfate ions such as a methylsulfate ion and an ethylsulfate ion; a hydrogensulfate ion; a borate ion; alkylphosphate ions and dialkylphosphate ions such as a diethylphosphate ion and a methylhydrogenphosphate ion; pyrophosphate ions such as a trimethylpyrophosphate ion; carboxylate ions such as an acetate ion, a propionate ion, a valerate ion, a citrate ion, a maleate ion, a fumarate ion, a lactate ion, a succinate ion, a tartarate ion, and a benzoate ion, wherein a carboxylate ion having a carboxyl group and a hydroxyl group is suitable for use; a carbonate ion; a hydrogencarbonate ion; and a hydroxide ion. Among the above, a halogen anion, a sulfonate anion, or a carboxylate anion is preferable as the counter anion, and a halogen anion is still more preferable, and a chlorine ion is particularly preferable.

The compounds represented by General Formula (1) and the compound represented by Formula (2) can be produced easily from known starting materials according to the following method disclosed in non-patent documents such as E. B. K Nott, *J. Chem. Soc.*, p. 4762 (1952), ibid p. 949 (1955), Kawakami et al., *J. Med. Chem.*, p. 3151 (1997), and K. Pudhom, *Heterocycles*, p. 207 (2009), which are incorporated herein by reference.

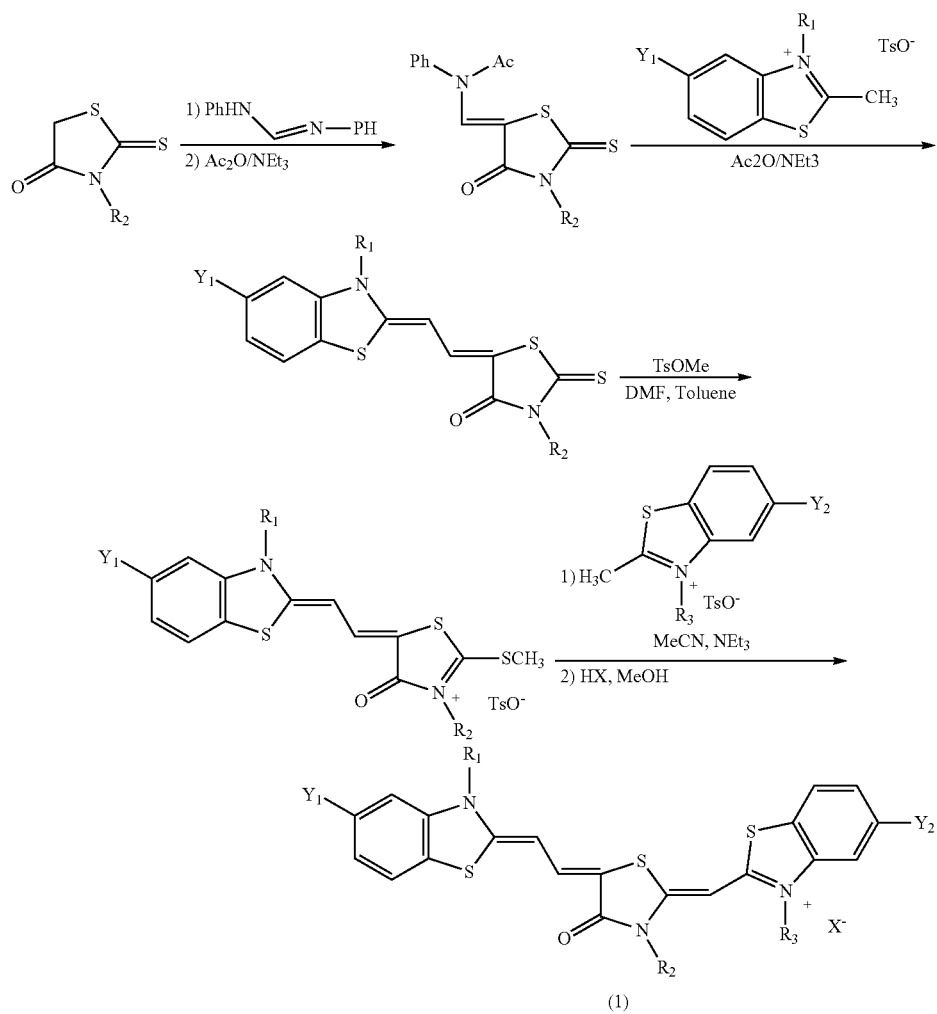
Typical examples of rhodacyanine compounds represented by General Formula (1) according to the invention include, but are not limited to, the compounds shown below.
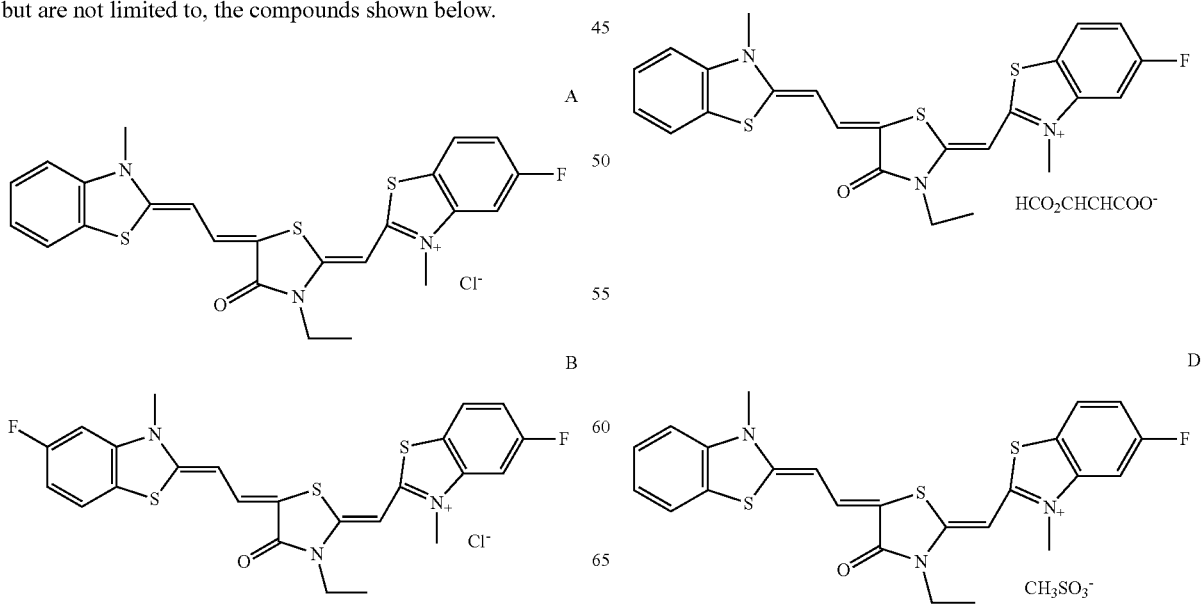

E
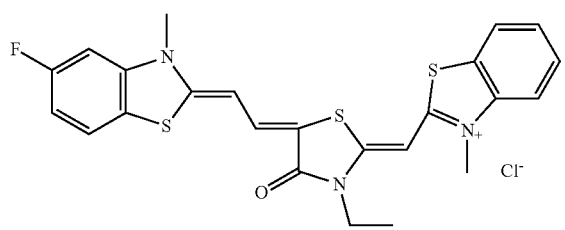

F
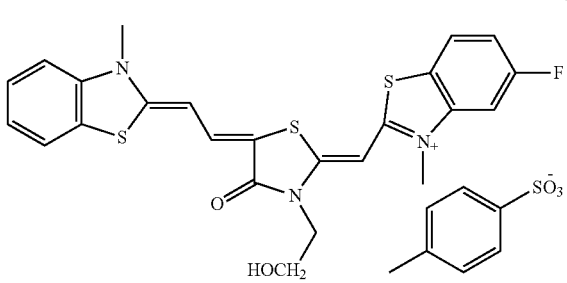

G
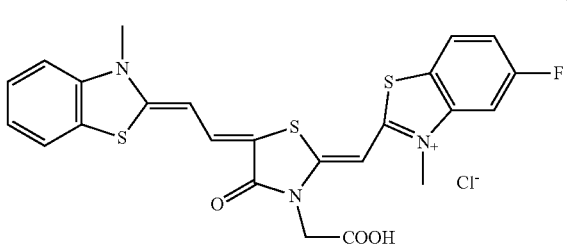

H
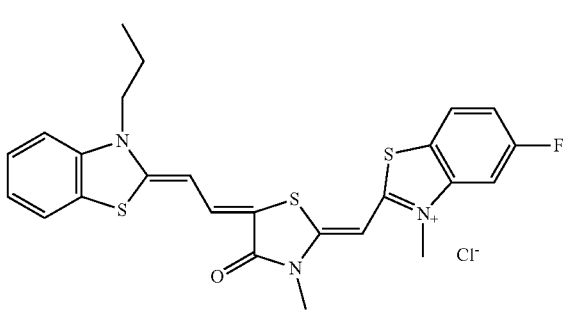

I
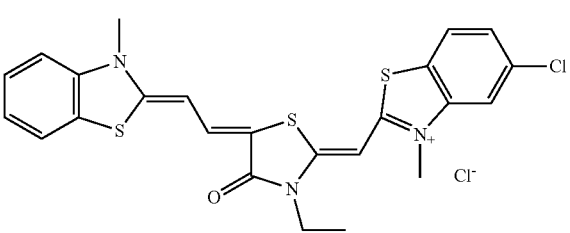

J
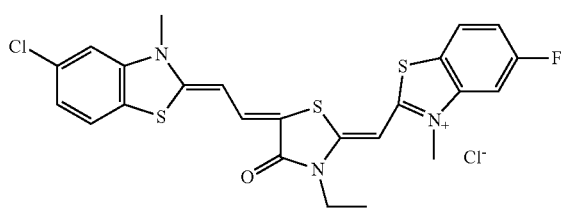

K
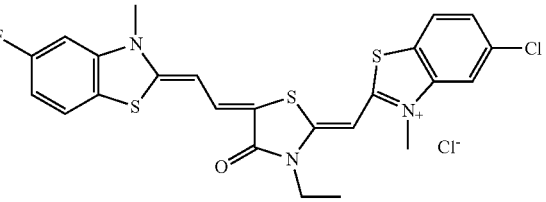

L

The pharmaceutical composition according to the invention includes the rhodacyanine derivative represented by General Formula (1) as an active ingredient, and can be used particularly as a pharmaceutical composition for treating leishmaniasis. The pharmaceutical composition for treating leishmaniasis according to the invention includes the rhodacyanine derivative and a pharmaceutically acceptable carrier. The pharmaceutical composition for treating leishmaniasis according to the invention may be administered together with a conventional anti-*leishmania* agent, such as pentostam, amphotericin B, or miltefosine, or may contain such a known anti-*leishmania* agent.

Examples of the pharmaceutically acceptable carrier in the pharmaceutical composition for treating leishmaniasis according to the invention include physiological saline and buffer solutions. The pharmaceutical composition for treating leishmaniasis may further include various known additive components such as diluents, stabilizers, perservatives, and tonicity agents. Examples of additive components include glucose, saccharose, lactose, ethyl alcohol, glycerin, mannitol, sorbitol, pentaerythritol, diethyleneglycol, dipropyleneglycol, polyethyleneglycol 400, other polyethyleneglycols, glycerin trilaurate, mono-, di-, and tri-glycerides of fatty acids, peptine, starch, alginic acid, xylol, talc, lycopodium, olive oil, peanut oil, castor oil, corn oil, safflower oil, sesami oil, sunflower oil, gelatin, lecithin, silica, cellulose, methylcellulose, hydroxyethylcellulose, calcium stearate, calcium laurate, magnesium oleate, calcium palmitate, cyclodextrins, emulsifying agents (for example, an ester of a saturated or unsaturated fatty acid having from 2 to 22 carbon atoms and a monohydric or polyhydric alcohol having from 2 to 20 carbon atoms such as glycol, glycerin, diethyleneglycol, pentaerythritol, ethyl alcohol, butyl alcohol, or octadecyl alcohol), and silicones such as methylpolysiloxane.

The pharmaceutically effective amount and administration method or means of the pharmaceutical composition for treating leishmaniasis according to the invention vary depending on the type of *leishmania* protozoa, the parasitic site, the seriousness of the disease, the therapeutic method, the age, weight, sex, and health condition of the patient, and the genetic and racial background of the patient. The dose of the pharmaceutical composition for treating leishmaniasis according to the invention, in terms of active ingredient amount, is generally from 1 to 2,000 mg/day/70 kg body weight, and is more generally from 50 to 500 mg/day/70 kg body weight. Examples of preferable dosage forms of the pharmaceutical composition for treating leishmaniasis according to the invention include a liquid formulation in which the rhodacyanine derivative according to the invention and optionally the additional components described above are dissolved in a 5% by mass glucose aqueous solution, a gel formulation, and an ointment. Examples of preferable administration methods for the pharmaceutical composition for treating leishmaniasis according to the invention include intravenous administration, intraperitoneal administration, subcutaneous injection, oral dosage, and application to the skin.

The method of treating leishmaniasis according to the invention includes administering, to a patient infected with *leishmania* or suspected to be infected with *leishmania*, the pharmaceutical composition for treating leishmaniasis containing the rhodacyanine derivative represented by General Formula (1), preferably represented by Formula (2), and a pharmaceutically acceptable carrier.

The pharmaceutical composition for treating leishmaniasis according to the invention has high selective toxicity against parasitic leishmaniasis. Examples of the leishmaniasis include cutaneous leishmaniasis, visceral leishmaniasis, and mucocutaneous leishmaniasis. The pharmaceutical composition for treating *leishmania* infection according to the invention has particularly high activity against visceral leishmaniasis. Therefore, it is particularly preferable that the pharmaceutical composition for treating leishmaniasis according to the invention is used for treating visceral leishmaniasis.

Examples of the present invention are described below. However, the technical scope of the invention is not limited to the examples.

EXAMPLES

Synthesis Example 1

Synthesis of 2-((3-ethyl-5-(2-(3-methylbenzo[d]thiazole-2(3H)-ylidene)ethylidene)-4-oxothiazolidine-2-ylidene)methyl-5-fluoro-3-methylbenzo[d]thiazole-3-ium chloride (Compound A)

Under an argon atmosphere, a mixture of 0.5 g (1.5 mmol) of 1-(3-ethyl-5-(2-(3-methylbenzo[d]thiazole-2(3H)-ylidene)ethylidene))-2-thioxo-4-oxothiazolidine, 0.84 g (4.5 mmol) of methyl p-toluenesulfonate, and 1.5 mL of DMF was stirred in toluene at 115° C. for 6 hours. After the mixture was cooled to ambient temperature, a liquid obtained by adding 0.51 g (1.5 mmol) of 5-fluoro-3-methylbenzo[d]thiazole-3-ium p-toluenesulfonate to 50 mL acetonitrile was added to the mixture. The resultant mixture was stirred for 12 hours at 75° C. The precipitate formed was collected and washed with acetonitrile and ethyl acetate to give 0.64 g of a tosylate as a dark-green solid. The yield was 65.8%. The analytical values of the obtained solid are as described below:

$^1$H NMR (400 MHz, DMSO-$d_6$) δ: 8.20 (dd, J=8.8 and 5.2 Hz, 1H), 7.82 (d, J=7.7 Hz, 1H), 7.71(dd, J=9.9 and 2.1 Hz, 1H), 7.57(d, J=13.2 Hz, 1H), 7.49 (d, J=8.0 Hz, 2H), 7.42-7.18 (m, 4H), 7.11 (d, J=8.0 Hz, 2H), 6.69 (s, 1H), 5.90 (d, J=13.2 Hz, 1H), 4.15 (q, J=7.1 Hz, 1H), 3.96 (s, 3H), 3.65 (s, 3H), 2.29 (s, 3H), 1.29 (t, J=7.1 Hz, 3H);
MS(ESI$^+$) m/z: 482.1 [M$^+$]

0.5 g (0.76 mmol) of the above tosylate was stirred in 50 mL methanol at 80° C. for 30 minutes. Then, about 2.3 mL concentrated hydrochloric acid was slowly added to the mixture. After the mixture was stirred for 30 minutes, the precipitate was filtered and washed with methanol to give 0.39 g of 2-((3-ethyl-5-(2-(3-methylbenzo[d]thiazole-2(3H)-ylidene)ethylidene)-4-oxothiazolidine-2-ylidene)methyl-5-fluoro-3-methylbenzo[d]thiazole-3-ium chloride (Compound A) as a dark-green solid. The yield was 99%. The physical property values and analytical values of this compound are as described below:

Mp: 274.5-275.6° C.;
UV-vis (H$_2$O): λ(nm)(log ε/L mol$^{-1}$ cm$^{-1}$): 528(4.54), 356 (4.23);
IR ν (neat, cm$^{-1}$): 2972, 1685, 1525, 1471, 1376, 1362, 1314, 1276, 1198, 1055, 1033, 941, 891, 819, 747;
$^1$H NMR (400 MHz, DMSO-$d_6$) δ: 8.27 (dd, J=8.9 and 5.2 Hz, 1H), 7.83 (d, J=7.7 Hz, 1H), 7.75 (dd, J=9.9 and 2.3 Hz, 1H), 7.59 (d, J=13.2 Hz, 1H), 7.43-7.31 (m, 3H), 7.28 (t, J=6.0 Hz, 1H), 6.72 (s, 1H), 5.88 (d, J=13.2 Hz, 1H), 4.17 (q, J=7.1 Hz, 2H), 3.98 (s, 3H), 3.68 (s, 3H), 1.29 (t, J=7.1 Hz, 3H);
$^{13}$C NMR (125 MHz, DMSO-$d_6$) δ: 164.0, 163.4, 163.0, 161.5, 157.3, 141.6, 134.6, 127.5, 125.0, 124.2, 123.8, 122.6, 121.5, 113.6, 113.4, 112.4, 102.3, 102.1, 101.7, 90.9, 86.5, 34.8, 32.9, 12.4;
MS (ESI$^+$) m/z: 482.1 [M$^+$]Anal. calcd. for C$_{24}$H$_{21}$ClFN$_3$OS$_3$.2H$_2$O: C, 51.97; H, 5.04; N, 7.55. Found: C, 52.02; H, 4.55; N, 7.58.

Synthesis Example 2

Synthesis of 2-((3-ethyl-5-(2-(3-methylbenzo[d]thiazol-2(3H)-ylidene)ethylidene)-4-oxothiazolidin-2-ylidene)methyl)-5-fluoro-3-methylbenzo[d]thiazol-3-ium maleate (Compound C)

After dissolving Compound A, which was obtained in Synthesis Example 1, in methanol, the anion thereof was replaced with maleic acid according to an ordinary method to give 2-((3-ethyl-5-(2-(3-methylbenzo[d]thiazol-2(3H)-ylidene)ethylidene)-4-oxothiazolidin-2-ylidene)methyl)-5-fluoro-3-methylbenzo[d]thiazol-3-ium maleate (Compound C) as a dark-green solid. The physical property values and analytical values of this compound are as described below:

Mp: 260.1-260.8° C.;
UV-vis (H$_2$O): λ (nm) (log ε/L mol$^{-1}$ cm$^{-1}$): 526 (4.68), 355 (4.37);
IR ν (neat, cm$^{-1}$): 2972, 2937, 2866, 1684, 1526, 1472, 1376, 1360, 1346, 1314, 1275, 1198, 1055, 1032, 1013, 940, 891, 818, 747;
$^1$H NMR (400 MHz, DMSO-$d_6$) δ: 8.28 (dd, J=8.8 and 5.1 Hz, 1H), 7.99 (dd, J=9.9 and 1.9 Hz, 1H), 7.89 (d, J=7.8 Hz, 1H), 7.75 (d, J=13.2 Hz, 1H), 7.59 (d, J=8.2 Hz, 1H), 7.49 (dd, J=17.0 and 8.3 Hz, 2H), 7.33 (t, J=7.6 Hz, 1H), 6.78 (s, 1H), 6.03 (d, J=13.2 Hz, 3H), 4.19 (q, J=7.1 Hz, 2H), 4.06 (s, 3H), 3.78 (s, 3H), 1.27 (t, J=7.1 Hz, 3H);
MS (ESI$^+$) m/z: 482.3 [M$^+$].

Synthesis Example 3

Synthesis of 2-((3-ethyl-5-(2-(3-methylbenzo[d]thiazol-2(3H)-ylidene)ethylidene)-4-oxothiazolidin-2-ylidene)methyl)-5-fluoro-3-methylbenzo[d]thiazol-3-ium methanesulfonate (Compound D)

After dissolving Compound A, which was obtained in Synthesis Example 1, in methanol, the anion thereof was replaced with methanesulfonic acid according to an ordinary method to give 2-((3-ethyl-5-(2-(3-methylbenzo[d]thiazol-2(3H)-ylidene)ethylidene)-4-oxothiazolidin-2-ylidene)methyl)-5- fluoro-3-methylbenzo[d]thiazol-3-ium mesylate (Compound D) as a dark-green solid. The physical property values and analytical values of this compound are as described below:

Mp>300° C.;

UV-vis (H$_2$O): λ (nm) (log ε/L mol$^{-1}$ cm$^{-1}$): 524 (4.83), 355 (4.52); IR ν(neat, cm$^{-1}$): 2971, 2937, 1682, 1525, 1470, 1376, 1358, 1317, 1276, 1197, 1057, 1033, 939, 891, 819, 747;

$^1$H NMR (400 MHz, DMSO-d$_6$) δ: 8.29 (dd, J=8.8 and 5.2 Hz, 1H), 8.01 (dd, J=9.9 and 2.0 Hz, 1H), 7.90 (d, J=7.8 Hz, 1H), 7.76 (d, J=13.2 Hz, 1H), 7.61 (d, J=8.3 Hz, 1H), 7.49 (m, 2H), 7.34 (t, J=7.8 Hz, 1H), 6.77 (s, 1H), 6.05 (d, J=13.2 Hz, 1H), 4.19 (q, J=7.1 Hz, 2H), 4.05 (s, 3H), 3.77 (s, 3H), 2.29 (s, 3H), 1.26 (t, J=7.1 Hz, 3H);

MS (ESI$^+$) m/z: 483.2 [M$^+$].

Example 1

(1) Culture of *Leishmania* Protozoa

In this test, *Leishmania donovani* (*L. Don*, MHOM/ET/67/L82 strain) was used. The protozoa were maintained in the Syrian Golden hamster, and amastigotes were collected from the spleen of an infected hamster. A SM medium supplemented with 10% heat-inactivated fetal bovine serum was used in the experiment, and the pH was adjusted to 5.4. The protozoa were grown at 37° C. under an atmosphere having a CO$_2$ concentration of 5%.

(2) *Leishmania* Protozoa Proliferation Inhibition Test

The activity with respect to inhibition of the proliferation of *leishmania* protozoa was studied for Compounds A, C, and D according to the invention for test, and for MKT-077, Compound X, and miltefosine (positive compound, existing drug) as comparative compounds. The structures of the compounds are as shown below. Each compound was dissolved in DMSO to give a test solution having a predetermined concentration.

A

C

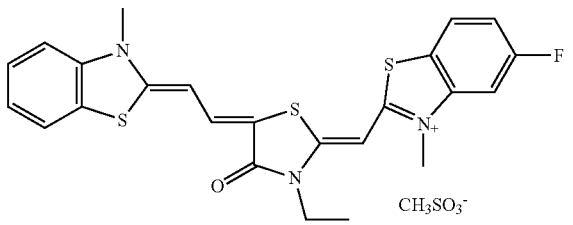

D

MKT-077

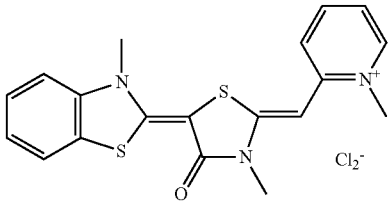

X

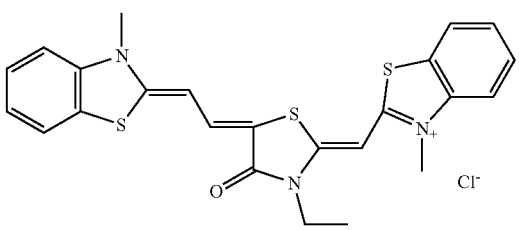

Each of the compounds to be used in the test was dissolved in DMSO to give a test solution having a concentration of 10 mg/mL. Assays were performed in 96-well culture plates, with each well containing 100 μL of the culture medium containing 10$^5$ amastigotes with or without the test compound at a predetermined serial dilution. The test was conducted twice.

After incubating the culture plates for 72 hours in an incubator, proliferation inhibiting activity was assayed. The assay was conducted in the following manner. 10 μL of an Alamar Blue aqueous solution (12.5 mg resazurin dissolved in 100 mL of distilled water) was added to each well, and the plates were incubated for another 2 hours. Each culture plate was mounted on a microplate fluorometer, and irradiated with light at an excitation wavelength of 536 nm. The intensity of fluorescence at 588 nm was measured, and the residual ratios of *leishmania* protozoa in the group added with the test solution and in the control were calculated.

The 50% proliferation inhibitory concentration (IC$_{50}$) values were determined based on the residual ratios of protozoa obtained above, and the results are shown in Table 1.

(3) Rat L6 Cell Proliferation Inhibition Test

Rat-derived L6 cells (rat skeletal myoblast cells) were used. The cells were cultured at 37° C. at a CO$_2$ concentration of 5%, using, as a culture medium, a RPMI 1640 medium supplemented with 1% L-glutamine (200 mM) and 10% fetal bovine serum (FBS).

Each of the compounds to be tested was dissolved in DMSO to give a test solution having a concentration of 10 mg/mL.

96-well culture plates of which each well contained 4×10$^4$ cells in 100 μL of the culture medium were prepared. After 24 hours, a 3-fold dilution series was prepared according to an ordinary method by adding a medium containing the compound to be tested, and the test was conducted.

After incubating the culture plates for 72 hours in an incubator, the plates were inspected with respect to proliferation activity. The inspection was conducted as follows. 10 μL of the Alamar Blue aqueous solution as described above was added to each well, and the plates were incubated for another 2 hours. Then, the culture plates were mounted on a microplate fluorometer, and irradiated with light at an excitation wavelength of 536 nm. The intensity of fluorescence at 588 nm was measured, and the residual ratios of L6 cells in the group added with the test solution and in the control were calculated.

The 50% proliferation inhibitory concentration ($IC_{50}$) values were determined based on the residual ratios of cells obtained above, and the results are shown in Table 1. In Table 1, "ND" represents that the test was not conducted.

(4) Determination of Drug Efficacy Against *Leishmania*

The selective toxicity coefficient, which is used as an index of the selectivity against *leishmania* protozoa, was calculated according to the following equation, and the drug efficacy was evaluated. The selective toxicity coefficient of each compound is shown in Table 1.

Selective toxicity coefficient=($IC_{50}$ value of the test compound against rat *L*6 cells)/($IC_{50}$ value of the test compound against *leishmania* protozoa)

TABLE 1

| Compound | 50% Proliferation Inhibitory Concentration (μM) | | Selective Toxicity Coefficient |
| --- | --- | --- | --- |
| | $IC_{50}$ L. Don | $IC_{50}$ L-6 Cells | |
| Compound A | 0.011 | >173 | >15,000 |
| Compound C | 0.025 | 71.7 | 2,870 |
| Compound D | 0.020 | 84.5 | 4,220 |
| MKT-077 (Comparative Compound) | 0.25 | 115 | 450 |
| Compound X (Comparative Compound) | 0.052 | 125 | 2,400 |
| Miltefosine (Comparative Compound) | 0.43 | ND | — |

Compounds A, C, and D according to the invention exhibited far higher protozoa inhibitory activity and far higher selective toxicity coefficient than MKT-077, and higher activity and higher selective toxicity coefficient than Compound X having hydrogen atoms as $Y^1$ and $Y^2$ in Formula (1). Further, Compounds A, C, and D exhibited more than 10 times higher activity than miltefosine, which is an existing drug, and only a weak toxicity toward normal cells. That is, Compounds A, C, and D are assessed as effective anti-*leishmania* drug with less side-effects. Therefore, it is found that the introduction of a fluorine atom is important.

Example 2

*Leishmania* Protozoa Proliferation Inhibition Test in Macrophages

The inhibitory activity on the proliferation of *leishmania* protozoa in macrophages was examined for Compounds A and B according to the invention and comparative compounds MKT-077, Compound X, Compound Y, Compound Z, and miltefosine (positive compound, existing drug). The structures of the compounds are as shown below.

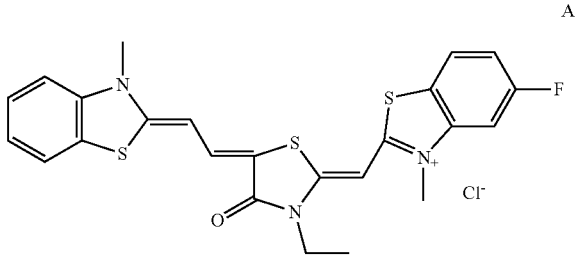

-continued

MKT-077

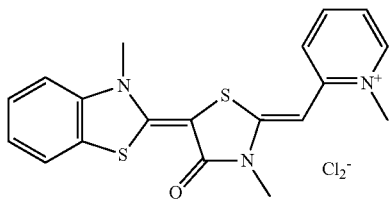

Peritoneal macrophages from NMRI mice are collected 1 day after stimulation of macrophage production with an intraperitoneal injection of 2 mL of a 2% potato starch suspension. The present test was conducted at 37° C. under an atmosphere having a $CO_2$ concentration of 5%. Each of the compounds to be used in the test was dissolved in DMSO to give a test solution having a predetermined concentration.

100 μL of a murine macrophage suspension ($4 \times 10^5$/mL) in a RPMI 1640 medium containing bicarbonate and N-2-hydroxyethylpiperazine-N'-2-ethanesulfonic acid (HEPES) and supplemented with 10% heat-inactivated fetal bovine serum (RPMI/FBS medium) was added to wells of 96-well culture plates. After 24 hours, 100 μL of a suspension containing amastigotes ($1.2 \times 10^6$/mL) was further added to each well, giving a suspension having a amastigotes/macrophages ratio of 3/1. The amastigotes were prepared in the same manner as above, and suspended in the RPMI/FBS medium. After 24 hours, the medium containing free amastigotes was removed, the cells were washed once with medium, and fresh media containing the test compound at serial dilutions (four 3-fold dilutions for each compound) were added to the wells. The growth of the protozoa in samples treated with the test-compound-containing media was compared with that of the control. Specifically, after 4 days of incubation, the samples were fixed with methanol, and thereafter stained with a 10% Giemsa solution. The $IC_{50}$ values were determined based on the number of infected macrophages.

The $IC_{50}$ value of each compound against leishmania protozoa is shown in Table 2.

TABLE 2

| | $IC_{50}$ L. Don (μM) |
|---|---|
| Compound A | 0.353 |
| Compound B | 0.452 |
| X (Comparative compound) | Could not be tested as the macrophages died |
| MKT-077 (Comparative compound) | Could not be tested as the macrophages died |
| Compound Y (Comparative compound) | Could not be tested as the macrophages died |
| Compound Z (Comparative compound) | Could not be tested as the macrophages died |
| Miltefosine (Comparative compound) | 0.811 |

As shown in Table 2, the compound according to the invention has a high ability to inhibit the proliferation of leishmania protozoa in macrophages, as compared to conventional anti-leishmania drugs as comparative compounds.

MKT-077 and Compounds Y and Z were all unable to be tested since the macrophages were killed by strong toxic effects exerted by these compounds in the present macrophage test. It is unexpected and surprising finding that such a harsh toxic effect against macrophages is reduced by introduction of a halogen atom, particularly a fluorine atom, according to the invention, and anti-leishmania activity is manifested.

Example 3

Anti-leishmania Activity Test Using Mice Infected with Leishmania

Compound A was used as the test compound in this test. Further, a pentostam-sensitive L. donovani (strain MHOM/ET/67/HU3) was used in this test, and the protozoa were maintained in Syrian Golden hamsters, and amastigotes were isolated from spleen cells of the infected hamster. Then, an inoculum containing $7.5 \times 10^7$ amastigotes/mL in RPMI 1640 was prepared. Female BALB/c mice (20 g) were infected with the amastigotes by intravenous injection at the tail vein on day 0. On day 7 after infection, one mouse was sacrificed, liver smears were methanol-fixed and Giemsa-stained, thereby confirming infection. The test compound was dissolved in an aqueous solution containing 10% ethanol and 5% glucose, and administered to the mice once a day for 5 days from day 7 to day 11. 3 days after the completion of the administration of the drug, livers were removed and weighed, and smears were methanol-fixed and then Giemsa-stained. The number of amastigotes (average value) per 500 liver cells was determined by counting, and the infection inhibition rate was determined based on the comparison thereof with mice that had not been treated with the drug. The results are shown in Table 3.

Infection inhibition rate (%)=$[1-(b-a)/(c-a)] \times 100$ a: Initial infection rate b: Infection rate in the mice treated with the test solution c: Infection rate in the control mice

TABLE 3

| | Dose (Intravenous Injection) (mg/kg/day) | Infection Inhibition Rate (%) |
|---|---|---|
| Compound A | 4.10 × 5 days | 97.1 |
| Compound A | 1.30 × 5 days | 94.9 |
| Compound A | 0.20 × 5 days | 16.1 |

As shown in Table 3, it was found that the compound according to the invention exhibits high infection-inhibition rate when administered by intravenous injection. Due to the easiness of synthesis thereof, the compound according to the invention is assessed as an inexpensive and effective anti-leishmania drug, and is effective as a single drug or a combined formulation with one or more other anti-leishmania drugs.

Therefore, it is confirmed that the pharmaceutical composition for treating leishmaniasis containing the rhodacyanine derivative according to the invention as an active ingredient has high selective toxicity and exhibits high activity and efficacy against leishmaniasis.

The disclosure of Japanese Patent Application No. 2009-251292 filed on Oct. 13, 2009 is herein incorporated by reference.

All publications, patent applications, and technical standards mentioned in this specification are herein incorporated by reference to the same extent as if each individual publication, patent application, or technical standard was specifically and individually indicated to be incorporated by reference.

The invention claimed is:

1. A rhodacyanine derivative represented by the following Formula (1):

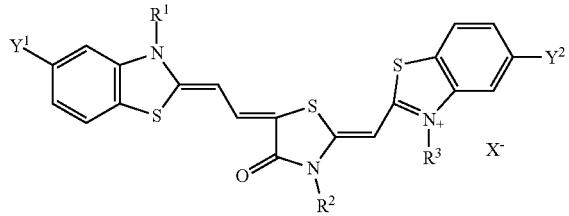

wherein, in Formula (1), $R^1$, $R^2$, and $R^3$ each independently represent an alkyl group which may be substituted; X represents a counter anion; and $Y^1$ and $Y^2$ are represented by at least one combination of $Y^1$ and $Y^2$ selected from the group consisting of:
- $Y^1$ represents a hydrogen atom and $Y^2$ represents a fluorine atom,
- $Y^1$ represents a fluorine atom and $Y^2$ represents a hydrogen atom,
- $Y^1$ represents a chlorine atom and $Y^2$ represents a fluorine atom,
- $Y^1$ represents a fluorine atom and $Y^2$ represents a chlorine atom, and
- $Y^1$ represents a fluorine atom and $Y^2$ represents a fluorine atom.

2. The rhodacyanine derivative according to claim 1, wherein, in Formula (1), $R^1$, $R^2$, or $R^3$ represents an alkyl group having from 1 to 8 carbon atoms, wherein the alkyl group may be substituted.

3. The rhodacyanine derivative according to claim 1, wherein, in Formula (1), $R^1$, $R^2$, or $R^3$ represents an alkyl group having at least one substituent selected from the group consisting of a halogen atom, a hydroxyl group, an oxo group, an alkyl group, an alkoxy group, and a carboxy group.

4. The rhodacyanine derivative according to claim 1, wherein, in Formula (1), X is selected from the group consisting of a halogen ion, a sulfonate ion, a sulfamate ion, a sulfate ion, a hydrogensulfate ion, a borate ion, an alkylphosphate ion, a dialkylphosphate ion, a pyrophosphate ion, a carboxylate ion, a carbonate ion, a hydrogencarbonate ion, and a hydroxide ion.

5. A rhodacyanine derivative represented by the following Formula (1):

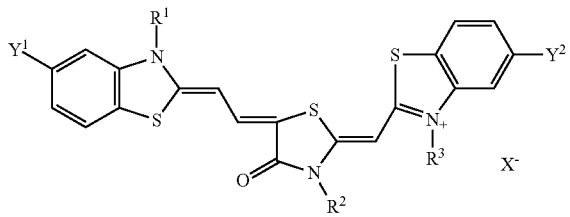

wherein, in Formula (1), $R^1$ and $R^3$ each represent a methyl group; $R^2$ represents an ethyl group; X represents a counterion; and $Y^1$ and $Y^2$ are represented by at least one combination of $Y^1$ and $Y^2$ selected from the group consisting of:
- $Y^1$ represents a hydrogen atom and $Y^2$ represents a fluorine atom,
- $Y^1$ represents a fluorine atom and $Y^2$ represents a hydrogen atom,
- $Y^1$ represents a chlorine atom and $Y^2$ represents a fluorine atom,
- $Y^1$ represents a fluorine atom and $Y^2$ represents a chlorine atom, and
- $Y^1$ represents a fluorine atom and $Y^2$ represents a fluorine atom.

6. The rhodacyanine derivative according to claim 1, wherein the rhodacyanine derivative is represented by the following Formula (2):

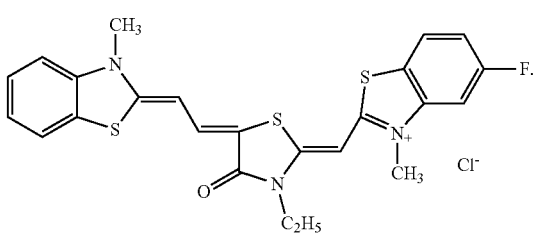

7. A pharmaceutical composition for treating leishmaniasis, comprising a rhodacyanine derivative represented by the following Formula (I) and a pharmaceutically acceptable carrier

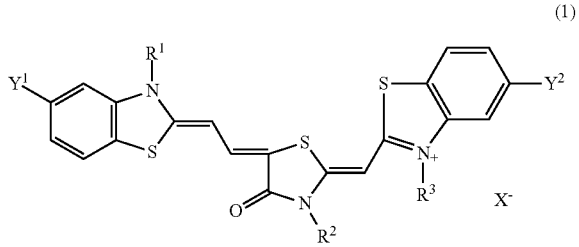

wherein, in Formula (1), $R^1$, $R^2$, and $R^3$ each independently represent an alkyl group which may be substituted; X represents a counter anion; and $Y^1$ and $Y^2$ are represented by at least one combination of $Y^1$ and $Y^2$ selected from the group consisting of:
- $Y^1$ represents a hydrogen atom and $Y^2$ represents a fluorine atom,
- $Y^1$ represents a fluorine atom and $Y^2$ represents a hydrogen atom,
- $Y^1$ represents a chlorine atom and $Y^2$ represents a fluorine atom,
- $Y^1$ represents a fluorine atom and $Y^2$ represents a chlorine atom, and
- $Y^1$ represents a fluorine atom and $Y^2$ represents a fluorine atom.

8. A method of treating leishmaniasis, comprising administering the pharmaceutical composition for treating leishmaniasis according to claim 7 to a patient infected with leishmania or suspected to be infected with leishmania.

9. The pharmaceutical composition for treating leishmaniasis according to claim 7, wherein, in Formula (1), $R^1$, $R^2$, or $R^3$ represents an alkyl group having from 1 to 8 carbon atoms, wherein the alkyl group may be substituted.

10. The pharmaceutical composition for treating leishmaniasis according to claim 7, wherein, in Formula (1), $R^1$, $R^2$, or $R^3$ represents an alkyl group having at least one substituent selected from the group consisting of a halogen atom, a hydroxyl group, an oxo group, an alkyl group, an alkoxy group, and a carboxy group.

11. The pharmaceutical composition for treating leishmaniasis according to claim 7, wherein, in Formula (1), X is selected from the group consisting of a halogen ion, a sulfonate ion, a sulfamate ion, a sulfate ion, a hydrogensulfate ion, a borate ion, an alkylphosphate ion, a dialkylphosphate ion, a pyrophosphate ion, a carboxylate ion, a carbonate ion, a hydrogencarbonate ion, and a hydroxide ion.

12. The pharmaceutical composition for treating leishmaniasis according to claim 7, wherein in Formula (1), $R^1$ and $R^3$ each represent a methyl group; and $R^2$ represents an ethyl group.

13. The pharmaceutical composition for treating leishmaniasis according to claim 7, wherein the rhodacyanine derivative is represented by the following Formula (2):

14. The method of treating leishmaniasis according to claim 8, wherein, in Formula (1), $R^1$, $R^2$, or $R^3$ represents an alkyl group having from 1 to 8 carbon atoms, wherein the alkyl group may be substituted.

15. The method of treating leishmaniasis according to claim 8 wherein, in Formula (1), $R^1$, $R^2$, or $R^3$ represents an alkyl group having at least one substituent selected from the group consisting of a halogen atom, a hydroxyl group, an oxo group, an alkyl group, an alkoxy group, and a carboxy group.

16. The method of treating leishmaniasis according to claim 8, wherein, in Formula (1), X is selected from the group consisting of a halogen ion, a sulfonate ion, a sulfamate ion, a sulfate ion, a hydrogensulfate ion, a borate ion, an alkylphosphate ion, a dialkylphosphate ion, a pyrophosphate ion, a carboxylate ion, a carbonate ion, a hydrogencarbonate ion, and a hydroxide ion.

17. The method of treating leishmaniasis according to claim 8, wherein in Formula (1), $R^1$ and $R^3$ each represent a methyl group; and $R^2$ represents an ethyl group.

18. The method of treating leishmaniasis according to claim 8, wherein the rhodacyanine derivative is represented by the following Formula (2):

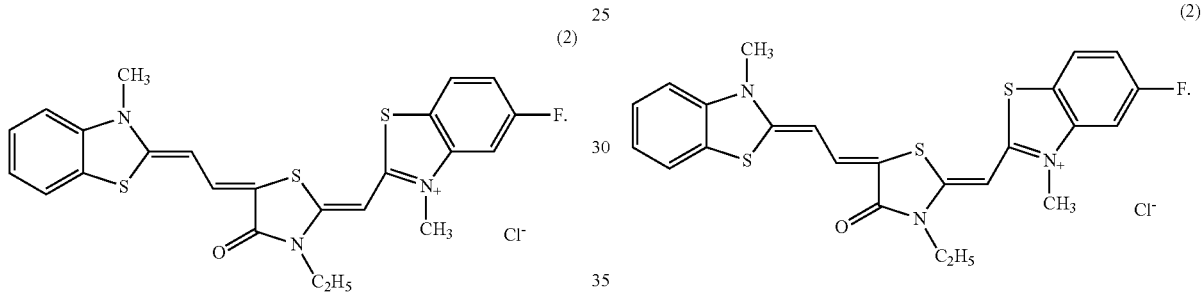

* * * * *